(12) United States Patent
Ugamura et al.

(10) Patent No.: US 6,726,811 B2
(45) Date of Patent: Apr. 27, 2004

(54) METHOD OF PURIFYING N-(2-HYDROXYETHY)-2-PYRROLIDONE

(75) Inventors: Shukichi Ugamura, Osaka-fu (JP); Hideto Sugiura, Kanagawa-ken (JP); Hitoshi Yano, Osaka-fu (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/105,447

(22) Filed: Mar. 26, 2002

(65) Prior Publication Data

US 2002/0139657 A1 Oct. 3, 2002

(30) Foreign Application Priority Data

Mar. 27, 2001 (JP) .......................... 2001-089872

(51) Int. Cl.⁷ .................... B01D 3/14; C07D 207/267
(52) U.S. Cl. .............. 203/74; 203/80; 203/99; 203/DIG. 19; 548/552; 548/555
(58) Field of Search ................ 203/73, 74, 77, 203/78, 80, 99, DIG. 19, 100; 548/555, 552, 543, 551; 528/501, 388

(56) References Cited

U.S. PATENT DOCUMENTS

| | | | | |
|---|---|---|---|---|
| 2,669,570 A | * | 2/1954 | Schnizer | 548/552 |
| 2,775,599 A | * | 12/1956 | Puetzer et al. | 548/552 |
| 2,939,869 A | * | 6/1960 | Carlson | 548/555 |
| 2,964,535 A | * | 12/1960 | Clements | 548/555 |
| 4,501,902 A | * | 2/1985 | Cleary | 548/555 |
| 4,976,825 A | * | 12/1990 | Iwasaki et al. | 203/71 |
| 6,436,243 B1 | * | 8/2002 | Yamaguchi et al. | 203/2 |

FOREIGN PATENT DOCUMENTS

| JP | 2765629 | 8/1994 |
|---|---|---|
| JP | 3024414 | 8/1994 |
| JP | 2001-002638 | 1/2001 |
| JP | 2001-002640 | 1/2001 |

* cited by examiner

*Primary Examiner*—Virginia Manoharan
(74) *Attorney, Agent, or Firm*—Sherman & Shalloway

(57) ABSTRACT

A method for obtaining high purity N-(2-hydroxyethyl)-2-pyrrolidone satisfactory for use as an intermediate material for N-vinyl-2-pyrrolidone from a reaction liquid formed of a reaction between y-butyrolactone and 2-aminoethanol, i.e., a liquid containing N-(2-hydroxyethyl)-2-pyrrolidone, compounds having boiling points lower than that of N-(2-hydroxyethyl)-2-pyrrolidone and compounds having boiling points higher than that of N-(2-hydroxyethyl)-2-pyrrolidone. The method is characterized by distilling said reaction liquid using a distillation column, whereby obtaining a liquid containing the compounds having the lower boiling points than that of N-(2-hydroxyethyl)-2-pyrrolidone and N-(2-hydroxyethyl)-2-pyrrolidone as a distillate liquid from the column top and a liquid containing compounds having boiling points higher than that of N-(2-hydroxyethyl)-2-pyrrolidone as a bottom liquid.

7 Claims, 2 Drawing Sheets

METHOD OF PURIFYING N-(2-HYDROXYETHY)-2-PYRROLIDONE

TECHNICAL FIELD

This invention relates to a method of purifying N-(2-hydroxyethyl)-2-pyrrolidone. N-vinyl-2-pyrrolidone, which is derived through intramolecular dehydration reaction of N-(2-hydroxyethyl)-2-pyrrolidone, is useful as starting monomer for poly-N-vinyl-2-pyrrolidone which has wide variety of utilities as a starting material for pharmaceuticals, food additives and cosmetics.

BACKGROUND ART

As a method of preparing N-(2-hydroxyethyl)-2-pyrrolidone, one comprising ring-opening and adding y-butyrolactone to 2-aminoethanol in liquid phase to form 4-hydroxy-N-(2-hydroxyethyl)-butanamide intermediate product, and then heating said intermediate product to cause its intramolecular dehydration reaction, while using water as the catalyst [Official Patent Gazettes of JP1972-21420 B, JP1974-20585 B and JP1979-22973 B (=U.S. Pat. No. 3,867,405)] is known.

Reaction products of the above method have complex composition composed of N-(2-hydroxyethyl)-2-pyrrolidone, water formed of the dehydration reaction, compounds having lower boiling points than N-(2-hydroxyethyl)-2-pyrrolidone (hereafter referred to as low-boiling component) and compounds having higher boiling points than N-(2-hydroxyethyl)-2-pyrrolidone (hereafter referred to as high-boiling component). Hence, for obtaining high purity (at the lowest 99.9% by weight) N-(2-hydroxyethyl)-2-pyrrolidone from the reaction products by removing the high-boiling component and low-boiling component, purification steps such as distillation is necessary. However, none of above cited Official Patent Gazettes contained any disclosure on a method for recovering high purity N-(2-hydroxyethyl)-2-pyrrolidone from said reaction products.

Whereas, as for N-methyl-2-pyrrolidone which is one of pyrrolidones but has entirely different physical properties from those of N-(2-hydroxyethyl)-2-pyrrolidone, methods of purification and recovery thereof have been disclosed in many Official Gazettes.

JP2,785,629 and JP3,024,414 disclose a production process of pyrrolidones characterized by distilling the low-boiling component off from the top of a first distillation column.

JP Kokai (laid-open) Gazette 2001-2638 A discloses a production process of high purity pyrrolidones, which comprises distilling the low-boiling component including unreacted amine and water off from the top of a first distillation column, setting the bottom liquid temperature of the first distillation column at 90–200° C. and the average residence time of the bottom liquid, for 10 minutes to 8 hours; while extracting from the bottom of the same column the bottom liquid of an amount corresponding to 2–15% by weight of the pyrrolidones contained in the feed; and recovering the remaining part of the pyrrolidones as side cut. JP Kokai Gazette 2001-2640 A also discloses a production process of high purity pyrrolidones which comprises setting the bottom liquid temperature in the first distillation column at 90–200° C. and the average residence time of the bottom liquid, for 10 minutes to 8 hours, while removing from the bottom of the first distillation column the bottom liquid of an amount corresponding to 2–15% by weight of the pyrrolidones contained in the feed, distilling the low-boiling component and the remaining pyrrolidones off from the column top, then supplying said column top distillate to a second distillation column, and distilling the low-boiling component off from the column top and recovering the pyrrolidones from the bottom of said column.

DISCLOSURE OF INVENTION

Thus, there is no prior art which disclosed a method for obtaining high purity N-(2-hydroxyethyl)-2-pyrrolidone of little low-boiling component content, which serves as an intermediate material to be used for synthesis of N-vinyl-2-pyrrolidone.

Gamma-butyrolactone, which is one of starting materials of N-(2-hydroxyethyl)-2-pyrrolidone, exhibits inert behavior during synthesis of N-vinyl-2-pyrrolidone. When y-butyrolactone remains in N-(2-hydroxyethyl)-2-pyrrolidone, most of it remains also during synthesis of N-vinyl-2-pyrrolidone.

Boiling temperature of y-butyrolactone is close to that of synthesized N-vinyl-2-pyrrolidone, and their separation in later purification step is difficult. In consequence, it provides a cause for lowering purity and increasing purification costs of resulting N-vinyl-2-pyrrolidone.

On the other hand, when 2-aminoethanol, which also is one of starting materials for N-(2-hydroxyethyl)-2-pyrrolidone, remains in N-(2-hydroxyethyl)-2-pyrrolidone, various heterocyclic amines are side produced during synthesis of N-vinyl-2-pyrrolidone, to cause coloring or unpleasant odor of resulting N-vinyl-2-pyrrolidone.

We tried purification of N-(2-hydroxyethyl)-2-pyrrolidone by distillation, referring to those processes described in Official Gazettes cited earlier, but could not obtain through any of those processes N-(2-hydroxyethyl)-2-pyrrolidone of high purity fully satisfactory for use as the intermediate material for N-vinyl-2-pyrrolidone.

In particular, under the operation conditions and bottom liquid temperature conditions as given in JP 2001-2638 A and JP 2001-2640 A, N-(2-hydroxyethyl)-2-pyrrolidone which was useful as a starting material of N-vinyl-2-pyrrolidone was not obtained at all. Presumably the operation conditions as described in the cited Kokai Gazettes are not applicable to production of N-(2-hydroxyethyl)-2-pyrrolidone because its physical properties largely differ from those of 2-pyrrolidones or N-alkyl-pyrrolidones which are the object compounds of the inventions described in those Gazettes. For example, for attaining the bottom liquid temperature of 90–200° C. following the descriptions in those Gazettes, inside pressure of the column needs to be kept no higher than 6.67 hPa (5.0 mmHg). In that occasion the column top temperature becomes about 10° C., and costs for cooling the condenser notably increase to bring about economical disadvantage.

After extensive studies, we came to discover: (1) because N-(2-hydroxyethyl)-2-pyrrolidone has higher boiling point than N-alkyl-pyrrolidones, the object compounds named in the cited Gazettes, generally high temperature operations inside the distillation column are inevitable; (2) because the high-boiling compounds in the reaction liquid have different structures from those in the processes of the cited Gazettes and have high reactivity, a part of the high-boiling component contained in the reaction liquid composition at the production time of N-(2-hydroxyethyl)-2-pyrrolidone undergoes pyrolysis during the distillative purification to form γ-butyrolactone or 2-aminoethanol; (3) according to the processes as described in the cited Gazettes, accompanying of such γ-butyrolactone or 2-aminoethanol, which are formed of pyrolysis, to N-(2-hydroxyethyl)-2-pyrrolidone is unavoidable; and (4) those phenomena are the causes why N-(2-hydroxyethyl)-2-pyrrolidone of high purity fully satisfactory for use as the intermediate material for N-vinyl-2-pyrrolidone cannot be obtained.

From the above-acquired knowledge, it is clear that recovery of N-(2-hydroxyethyl)-2-pyrrolidone from the products of the process described in said JP1979-22973 B (=U.S. Pat. No. 3,867,405) by means of conventional distillation operations is liable to invite purity degradation of N-(2-hydroxyethyl)-2-pyrrolidone due to pyrolysis of the high-boiling component contained in the reaction liquid.

Accordingly, therefore, an object of the present invention is to provide a method for obtaining high purity N-(2-hydroxyethyl)-2-pyrrolidone which is fully satisfactory for use as an intermediate material for N-vinyl-2-pyrrolidone, from a reaction liquid resulting from reacting γ-butyrolactone with 2-aminoethanol and containing N-(2-hydroxyethyl)-2-pyrrolidone, low-boiling component and high-boiling component.

We have made concentrative research work with the view to accomplish the above object, to find that high purity N-(2-hydroxyethyl)-2-pyrrolidone can be efficiently and stably recovered by, in the occasion of the recovery through distillation of the liquid resulting from reacting γ-butyrolactone with 2-aminoethanol and containing N-(2-hydroxyethyl)-2-pyrrolidone, low-boiling component and high-boiling component, first removing the high-boiling component and then removing the low-boiling component and remaining high-boiling component, whereby inhibiting blending of impurities formed of pyrolysis of the high-boiling component into the object product.

Thus, according to the invention a method of purifying N-(2-hydroxyethyl)-2-pyrrolidone is provided, which process comprising purifying a liquid resulting from reacting γ-butyrolactone with 2-aminoethanol and containing N-(2-hydroxyethyl)-2-pyrrolidone, compounds having lower boiling points than that of N-(2-hydroxyethyl)-2-pyrrolidone, and compounds having higher boiling points than that of N-(2-hydroxyethyl)-2-pyrrolidone, by distillation using a distillation column, said process being characterized by obtaining a liquid containing said compounds having lower boiling points than that of N-(2-hydroxyethyl)-2-pyrrolidone and N-(2-hydroxyethyl)2-pyrrolidone as the liquid distillate from the column top, while obtaining a liquid containing the compounds having boiling points higher than that of N-(2-hydroxyethyl)-2-pyrrolidone as the bottom liquid.

According to the method of this invention, said distillation column (which is hereafter referred to as the first distillation column) is preferably operated under the conditions of 200–260° C. in bottom liquid temperature and 6.67–66.7 hPa (5.0–50 mmHg) in column top pressure.

According to the method of the invention, the distillate liquid from the first distillation column is distilled using a second distillation column, whereby obtaining a liquid containing the compounds having boiling points lower than that of N-(2-hydroxyethyl)-2-pyrrolidone as the distillate liquid from the column top, and concurrently, purified N-(2-hydroxyethyl)-2-pyrrolidone as a side cut from a position of the distillation column higher than the bottom.

According to the method of the present invention, said distillate liquid distilled off from the first distillation column is distilled using the second distillation column, whereby obtaining a liquid containing the compounds having boiling points lower than that of N-(2-hydroxyethyl)-2-pyrrolidone as the distillate liquid from the column top and a liquid containing N-(2-hydroxyethyl)-2-pyrrolidone as the bottom liquid; and then said bottom liquid is distilled using a third distillation column to provide purified N-(2-hydroxyethyl)-2-pyrrolidone as the distillate liquid.

In short, according to the invention high purity N-(2-hydroxyethyl)-2-pyrrolidone can be obtained by separating the high-boiling component, which undergoes pyrolysis to form γ-butyrolactone or 2-aminoethanol, from N-(2-hydroxyethyl)-2-pyrrolidone in the distillation step using the first distillation column (formation of pyrolyzed products in this step has no detrimental effect), and then distilling the separated N-(2-hydroxyethyl)-2-pyrrolidone using the second distillation column or the second and third distillation columns.

Brief Description of Drawings

Referring to the appended drawings.

Modes for Carrying Out the Invention

Figure 1:
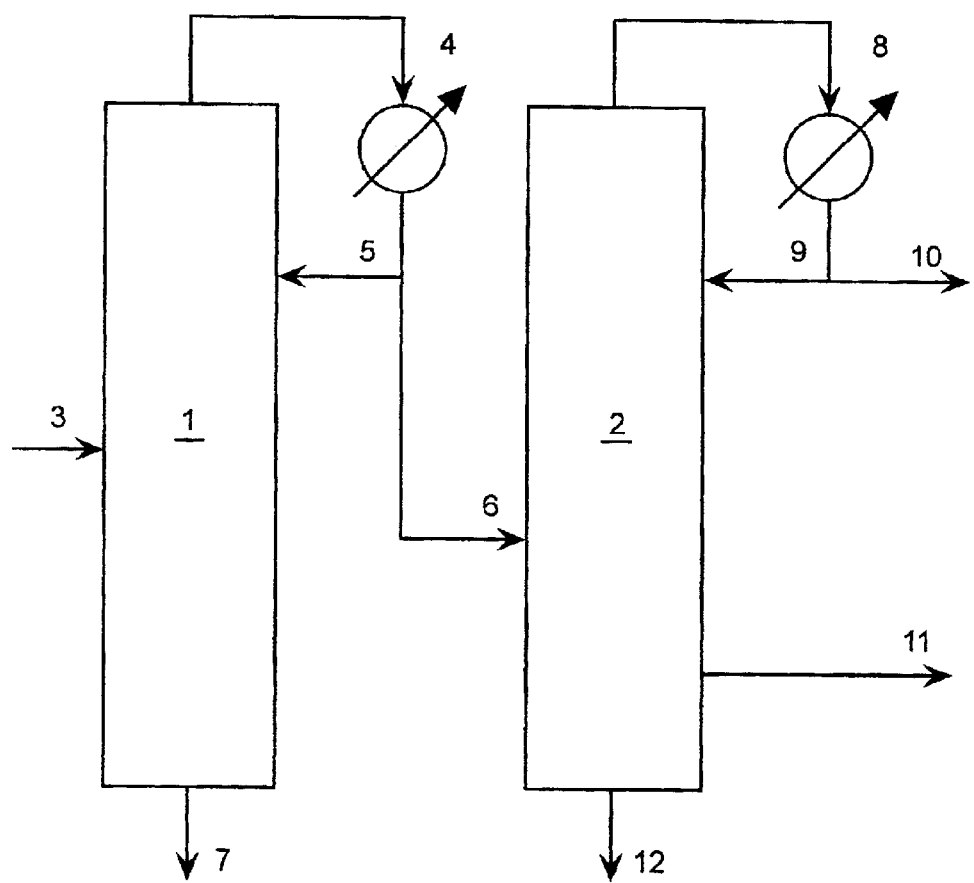
FIG. 1 is a plan view of an apparatus including two distillation columns, for practicing the method of purifying N-(2-hydroxyethyl)-2-pyrrolidone according to the present invention.

Hereinafter the invention is explained in further details referring to FIG. 1 in which 1 is a first distillation column, 2 is a second distillation column, 3 is a reaction liquid-feed line, 4 is a condenser, 5 is a reflux line, 6 is a feed line, 7 is an extraction line for the high-boiling component, 8 is a condenser, 9 is a reflux line, 10 is an extraction line for the low-boiling component, 11 is an extraction line for the side cut N-(2-hydroxyethyl)-2-pyrrolidone product, and 12 is an extraction line for the high-boiling component.

In the purification method of N-(2-hydroxyethyl)-2-pyrrolidone to which the present invention relates, the object liquid of distillation operations is a liquid mixture containing N-(2-hydroxyethyl)-2-pyrrolidone, low-boiling component and high-boiling component.

Said liquid can be obtained, for example, through the process disclosed in JP Kokoku (publication) Sho 54(1979)-22973 B (=U.S. Pat. No. 3,867,405). One specific example is N-(2-hydroxyethyl)-2-pyrrolidone-containing reaction liquid obtained by stirring γ-butyrolactone, 2-aminoethanol and water in a hermetically sealed pressure reactor to induce the ring-opening addition reaction, and further heating the system to cause intramolecular dehydration reaction, but method for obtaining such a reaction liquid is not especially limited to this.

In the present specification, high-boiling component refers to the substances having boiling points higher than that of N-(2-hydroxyethyl)-2-pyrrolidone; and low-boiling component, the substances having boiling points lower than that of N-(2-hydroxyethyl)-2-pyrrolidone.

As examples of the low-boiling component, γ-butyrolactone, 2-aminoethanol and water can be named, but the component is not limited to these.

Said reaction liquid is first fed into the first distillation column 1, through the reaction liquid feed line 3. From the top of said first distillation column, a liquid containing the low-boiling component (e.g., side products such as 2-pyrrolidone, γ-butyrolactone, 2-aminoethanol, water and the like) and N-(2-hydroxyethyl)-2-pyrrolidone is distilled off.

Within this distillation column, a part of the high-boiling component is pyrolyzed to form y-butyrolactone, 2-aminoethanol and the like which also are distilled off from the column top together with N-(2-hydroxyethyl)-2-pyrrolidone.

In the first distillation column, a part of the N-(2-hydroxyethyl)-2-pyrrolidone is discharged, together with the high-boiling component, through the high-boiling component extraction line 7 at the bottom of the column. The amount of so discharged N-(2-hydroxyethyl)-2-pyrrolidone may be 0.5–5.0% by weight, preferably 1.0–4.0% by weight, to the N-(2-hydroxyethyl)-2-pyrrolidone content in the feed liquid to the first distillation column.

The distillate containing the low-boiling component and N-(2-hydroxyethyl)-2-pyrrolidone, which leaves the column from the top of the first distillation column, is condensed at the condenser 4 and fed into the second distillation column 2 through the feed line 6, excepting a part thereof which is returned to the distillation column 1 via the reflux line 5.

At the second distillation column, the liquid containing the low-boiling component, e.g., γ-butyrolactone, 2-aminoethanol, water and the like, is distilled off from the column top, while a part of N-(2-hydroxyethyl)-2-pyrrolidone is withdrawn from the bottom of the column, together with the high-boiling component. The amount of the N-(2-hydroxyethyl)-2-pyrrolidone to be withdrawn is 0.5–5.0% by weight, preferably 1.0–4.0% by weight, to the N-(2-hydroxyethyl)-2-pyrrolidone content in the feed to the second distillation column. N-(2-hydroxyethyl)-2-pyrrolidone as the object product is obtained as a side cut. More specifically, the low-boiling component distilled off from the column top is condensed in the condenser 8 and discharged through line 10, except a part thereof which is returned to the second distillation column 2 via the reflux line 9. On the other hand, the high-boiling component is discharged through the extraction line 12, and the intended N-(2-hydroxyethyl)-2-pyrrolidone of very high purity is obtained as a side cut, from the line 11 positioned higher than the bottom of the column.

Figure 2:
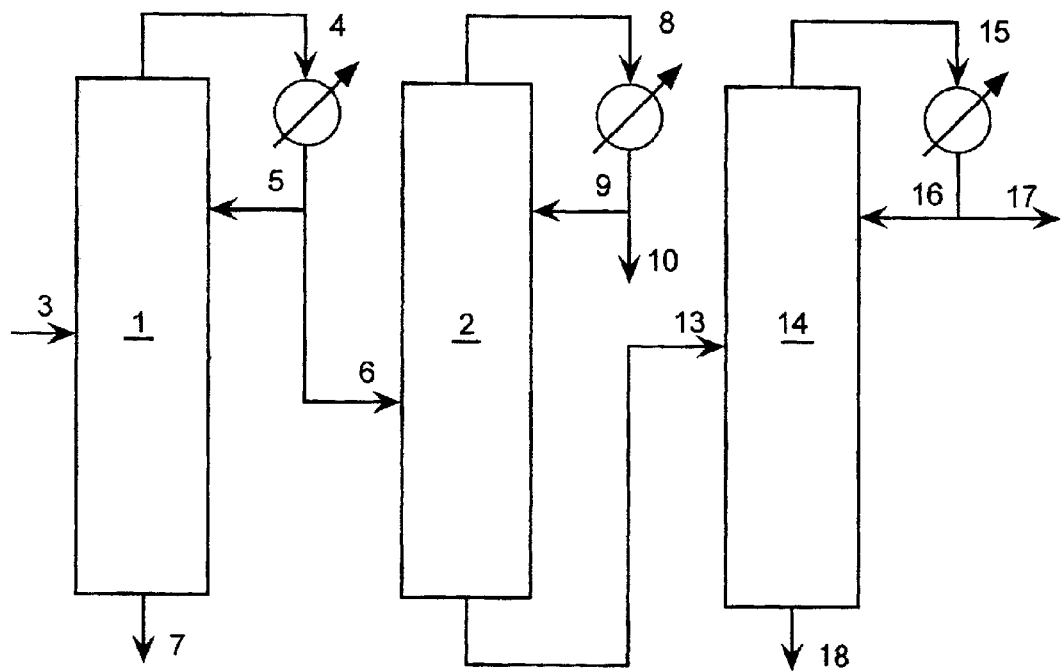
FIG. 2 is a plan view of an apparatus including three distillation columns, for practicing the method of purifying N-(2-hydroxyethyl)-2-pyrrolidone according to the present invention.

According to the invention, the intended high purity N-(2-hydroxyethyl)-2-pyrrolidone can be obtained also by a method using the purification apparatus as shown in FIG. 2, besides the one as illustrated by FIG. 1. In FIG. 2, 13 is a feed line, 14 is a third distillation column, 15 is a condenser, 16 is a reflux line, 17 is an extraction line for the product N-(2-hydroxyethyl)-2-pyrrolidone, and 18 is an extraction line for the bottom liquid. The reference numbers 1 to 10 denote the same parts as in FIG. 1.

In the method of FIG. 2, a liquid containing N-(2-hydroxyethyl)-2-pyrrolidone is supplied from the bottom of the second distillation column into the third distillation column 14 through line 13 and distilled. At the third distillation column 14, a part of N-(2-hydroxyethyl)-2-pyrrolidone which is contained in the feed liquid to said column is withdrawn from the bottom of the column through the bottom liquid extraction line 18. The amount of the withdrawn N-(2-hydroxyethyl)-2-pyrrolidone may be 0.5–5.0% by weight, preferably 1.0–4.0% by weight, to the N-(2-hydroxyethyl)-2-pyrrolidone content in the feed liquid to said third distillation column. On the other hand, from the column top a very high purity N-(2-hydroxyethyl)-2-pyrrolidone as condensed at the condenser 15 is obtained through the product extraction line 17.

N-(2-hydroxyethyl)-2-pyrrolidone is a compound having the igniting temperature of around 270° C. Because it is apt to be decomposed and ignited, it is preferred for safety to conduct the distillation at the bottom temperature not higher than 260° C. (It is the bottom liquid that comes to attain the highest temperature during distillation operations.) In particular, when the distillation is carried out at the bottom liquid temperature not higher than 250° C., decomposition of N-(2-hydroxyethyl)-2-pyrrolidone in the distillation columns 2 and 14 is strongly inhibited, and in consequence high purity N-(2-hydroxyethyl)-2-pyrrolidone can be obtained more easily.

The lower limit temperature of the bottom liquid is determined in consideration of the cost for cooling the condenser and decompressor capacity. It is preferably 200° C., in particular, 210° C.

The column top pressure in the first distillation column is preferably controlled within a range of 6.67–66.7 hPa (5.0–50.0 mmHg). Where the column top pressure is less than 6.67 hPa, cost for cooling the condenser increases, and when it exceeds 66.7 hPa, the bottom liquid temperature is liable to rise above 260° C., while it also depends on composition of the bottom liquid.

Number of plates in those distillation columns is not critical, while it may range from 3 to 30 theoretical plate number depending on reflux ratio in each step. Construction of the columns again is not subject to specific limitation, but for the purpose of keeping the bottom liquid temperature low under a same distillation pressure, packed tower-type distillation columns causing little pressure loss are convenient.

EXAMPLES

Hereinafter the present invention is more specifically explained with reference to its working examples, it being understood that the invention is not limited by the following examples, so long as the essence of the invention is not deviated.

In the working examples, gas chromatographic analyses were conducted under the following conditions:

Model: GC-14B Kabusiki Kaisha Shimadzu Seisakujo

Column: SPB-1 Capillary SUPELCO Inc.

GC sensitivity: $10^{1-2}$

Detector: FID

Example 1

A reactor was charged with γ-butyrolactone, 2-aminoethanol and water, to produce N-(2-hydroxyethyl)-2-pyrrolidone. The molar ratio of the 2-aminoethanol/γ-butyrolactone was 1.0, and that of the γ-butyrolactone/water was 1.1. The reaction temperature was 250° C. and the reaction time was 2 hours.

The resulting reaction product contained 73.0% of N-(2-hydroxyethyl)-2-pyrrolidone, 21.1% of low-boiling component (0.1% of 2-aminoethanol, 1.0% of γ-butyrolactone and 20.0% of water) and 5.9% of high-boiling component, the percentages being by weight. From this reaction product, purified N-(2-hydroxyethyl)-2-pyrrolidone was recovered in the following manner, using the apparatus as illustrated in FIG. 1.

The reaction product was supplied through the line 3, to a feed inlet positioned at an upper part of the fourth plate of a first distillation column having five plates (plate number). The distillation at the first distillation column was operated under the conditions of: pressure, 53.2 hPa (40 mmHg); bottom liquid temperature, about 250° C.; column top temperature, about 40° C., and the reflux ratio, 0.3.

From the bottom of the first distillation column, 2.0 wt % of the N-(2-hydroxyethyl)-2-pyrrolidone which was supplied to the same distillation column was extracted together with the high-boiling component through line 7, and from the top of the same column a liquid containing the low-boiling component and N-(2-hydroxyethyl)-2-pyrrolidone was obtained as the distillate liquid.

Then the distillate liquid from the top of the first distillation column was supplied to a 5-plated (plate number) second distillation column through the line 6. The operation conditions at the second distillation column were: pressure, 133 hPa (100 mmHg); bottom liquid temperature, about 230° C.; column top temperature, about 50° C.; and the reflux ratio, 2.0.

From the top of the second distillation column, distillate liquid containing the low-boiling component was recovered. From the bottom of the second distillation column, 1.0 wt % of the N-(2-hydroxyethyl)-2-pyrrolidone which was supplied to the second distillation column was extracted, and the object N-(2-hydroxyethyl)-2-pyrrolidone was recovered through line 11.

So recovered N-(2-hydroxyethyl)-2-pyrrolidone had a very high purity of 99.9 wt % (gas chromatography-analyzed value). According to impurity measurement of the product, its γ-butyrolactone (a low-boiling component) content was 120 ppm, and no 2-aminoethanol (a low-boiling component) or high-boiling component was detected.

Example 2

From a reaction mixture of identical composition with that acquired in Example 1, purified N-(2-hydroxyethyl)-2-pyrrolidone was recovered using the apparatus as illustrated in FIG. 2, in the following manner. The distillation at the first distillation column was operated in the same manner as in Example 1.

The distillate from the top of the first distillation column was supplied to a 5-plated (plate number) second distillation column through line 6. The distillation at the second distillation column was operated under the conditions of: pressure, 133 hPa (100 mmHg); bottom liquid temperature, about 230° C.; column top temperature, about 50° C.; and the reflux ratio, 2.0. While distilling the low-boiling component off from the column top, a liquid containing N-(2-hydroxyethyl)-2-pyrrolidone was recovered from the column bottom and supplied to a 5-plated (plate number) third distillation column through line 13.

At the third distillation column, the distillation was conducted under a reduced pressure of 13.3 hPa (10 mmHg), at a bottom liquid temperature of about 170° C. and the column top temperature of about 165° C. While a liquid containing 1.0 wt % of the N-(2-hydroxyethyl)-2-pyrrolidone, which was contained in the feed liquid to the third distillation column, was extracted from the column bottom through line 18, purified N-(2-hydroxyethyl)-2-pyrrolidone, the object product, was recovered from the column top.

Thus recovered N-(2-hydroxyethyl)-2-pyrrolidone had a very high purity of 99.9 wt % (gas chromatography-analyzed value). According to impurity measurement of the product, its γ-butyrolactone (a low-boiling component) content was 100 ppm, and no 2-aminoethanol (a low-boiling component) or high-boiling component was detected.

Example 3

Example 2 was repeated except the operating pressure at the first distillation column was raised to 133 hPa (100 mmHg). The column top temperature was about 60° C., and the bottom liquid temperature was about 270° C.

Whereby recovered N-(2-hydroxyethyl)-2-pyrrolidone had a very high purity of 99.8 wt % (gas chromatography-analyzed value). According to its impurity measurement, its γ-butyrolactone (a low-boiling component) content was 0.2 wt %, 2-aminoethanol (a low-boiling component) content was 220 ppm, and no high-boiling component was detected.

Comparative Example 1

A reaction mixture of identical composition with that acquired in Example 1 was treated in the following manner. First it was supplied into a 5-plated (plate number) first distillation column through a feed inlet provided at an upper part of the third plate. The distillation was operated under a reduced pressure of 133 hPa (100 mmHg), at the bottom liquid temperature of about 110° C., column top temperature of about 50° C. and the reflux ratio of 0.2.

From the column top 95% of the low-boiling component which was contained in the feed liquid to the first distillation column was distilled off, while recovering from the column bottom the bottom liquid containing N-(2-hydroxyethyl)-2-pyrrolidone and supplying it to a 10-plated (plate number) second distillation column.

The operation at the second distillation column was conducted under the conditions of: pressure, 133 hPa (100 mmHg); bottom liquid temperature, about 250° C.; column top temperature, about 50° C.; and the reflux ratio, 5.0. From the column top the distillate liquid containing low-boiling component was taken out and from the column bottom 5.0 wt % of the N-(2-hydroxyethyl)-2-pyrrolidone which was contained in the feed liquid to the second distillation column was withdrawn. The product N-(2-hydroxyethyl)-2-pyrrolidone was recovered from an upper part of the 8th plate as a side cut.

Purity of the recovered N-(2-hydroxyethyl)-2-pyrrolidone was lower than that of the product of Example 1. The gas chromatography-analyzed value was 97.4 wt %. According to impurity measurement of the product, γ-butyrolactone (a low-boiling component) content was 0.4 wt %, 2-aminoethanol (a low-boiling component) content was 5 ppm and high-boiling component content was 2.2 wt %.

Industrial Applicability

As has been described in detail, according to the method of this invention, the high-boiling component, which is readily pyrolyzed during distillation to form γ-butyrolactone, 2-aminoethanol and the like, is effectively removed. In consequence, high purity N-(2-hydroxyethyl)-2-pyrrolidone fully satisfactory as an intermediate material for preparing N-vinyl-2-pyrrolidone can be obtained.

We claim:

1. A method of purifying N-(2-hydroxyethyl)-2-pyrrolidone which comprises distilling a liquid resulting from reacting γ-butyrolactone with 2-aminoethanol, which liquid containing N-(2-hydroxyethyl)-2-pyrrolidone, compounds having lower boiling points than that of N-2-hydroxyethyl)-2-pyrrolidone, and compounds having higher boiling points than that of N-(2-hydroxyethyl)-2-pyrrolidone using a first distillation column and a second distillation column, characterized in that the liquid is distilled using the first distillation column, thereby recovering a distillate containing the compounds having lower boiling points than that of N-(2-hydroxyethyl)-2-pyrrolidone and N-(2-hydroxyethyl)-2-pyrrolidone as a condensate of vapor from the first distillation column top, while removing a liquid containing the compounds having boiling points higher than that of N-(2-hydroxyethyl)-2-pyrrolidone as a bottom liquid, and then the distillate recovered from the first distillation column is distilled using the second distillation column, thereby removing a distillate containing the compounds having boiling points lower than that of N-(2-hydroxyethyl)-2-pyrrolidone as a condensate of vapor from the second distillation column top, and concurrently recovering N-(2-hydroxyethyl)-2-pyrrolidone as a side cut from a position of the second distillation column higher than the bottom thereof.

2. The method according to claim 1, in which said first distillation column is operated at the bottom liquid temperature of 200–260° C.

3. The method according to claim 1, in which said first distillation column is operated at a column top pressure of 6.67–66.7 hPa (5.0–50 mmHg).

4. A method of purifying N-(2-hydroxyethyl)-2-pyrrolidone which comprises distilling a liquid resulting from reacting γ-butyrolactone with 2-aminoethanol, which liquid containing N-(2-hydroxyethyl)-2-pyrrolindone, compounds having lower boiling points than that of N-(2-hydroxyethyl)-2-pyrrolidone, and compounds having higher boiling points than that of N-(2-hydroxyethyl)-2-pyrrolidone using a first distillation column and a second distillation column, characterized in that the liquid is distilled using the first distillation column, thereby recovering a distillate containing the compounds having lower boiling points than that of N-(2-hydroxyethyl)-2-pyrrolidone and N-(2-hydroxyethyl)-2-pyrrolidone as a condensate of vapor from the first distillation column top, while removing a liquid containing the compounds having boiling points higher than that of N-(2-hydroxyethyl)-2-pyrrolidone as a bottom liquid, and then the distillate recovered from the first distillation column is distilled using the second distillation column, thereby removing a distillate containing the compounds having boiling points lower than that of N-(2-hydroxyethyl)-2-pyrrolidone as a condensate of vapor from the second distillation column top and recovering a liquid containing N-(2-hydroxyethyl)-2-pyrrolidone as a bottom liquid.

5. The method according to claim 4, in which the bottom liquid is distilled using a third distillation column to recover N-(2-hydroxyethyl)-2-pyrrolidone as a condensate vapor from the column top.

6. The method according to claim 4, in which said first distillation column is operated at the bottom liquid temperature of 200–260° C.

7. The method according to claim 4, in which said first distillation column is operated at a column top pressure of 6.67–66.7 hPa (5.0–50 mmHg).

* * * * *